United States Patent [19]

Vanderveen et al.

[11] 4,224,414
[45] Sep. 23, 1980

[54] FERMENTATION APPARATUS AND METHOD

[75] Inventors: John W. Vanderveen; Emil A. Malick, both of Bartlesville, Okla.

[73] Assignee: Phillips Petroleum Company, Bartlesville, Okla.

[21] Appl. No.: 887,279

[22] Filed: Mar. 16, 1978

[51] Int. Cl.² .............................................. C12M 1/04
[52] U.S. Cl. .................................. 435/313; 435/314; 435/315; 261/93; 415/203
[58] Field of Search ............... 195/109, 142, 143, 135; 261/87, 93; 435/313, 314, 315, 243

[56] References Cited

U.S. PATENT DOCUMENTS

| 3,460,810 | 8/1969 | Müller | 366/263 |
| 3,572,661 | 3/1971 | Müller | 261/93 X |
| 3,577,868 | 5/1971 | Müler | 55/178 |
| 3,625,834 | 12/1971 | Müller | 195/109 |
| 3,693,325 | 9/1972 | Müller | 55/178 |
| 3,752,742 | 8/1973 | Jaekel et al. | 195/109 |
| 3,986,934 | 10/1976 | Müller | 195/142 |

OTHER PUBLICATIONS

Kirk-Othmer, Encyclopedia of Chemical Technology, 2nd Ed., vol. 16, John Wiley & Sons, 1968, pp. 730–737.
Arthur F. Taggart, Elements of Ore Dressing, John Wiley & Sons, 1951, pp. 312–314.
A. J. Stepanoff, Centrifugal and Axial Flow Pumps, Theory, Design and Application, John Wiley & Sons, 1948, pp. 48–52, 105–106, and 236–237.

Primary Examiner—Robert J. Warden

[57] ABSTRACT

A centrifugal pump adapted for use in a fermenter is provided. The fermenter includes an outer vessel which has mounted therein a generally centrally located draft tube. A centrifugal pump is mounted adjacent to one end of the draft tube and is operably connected to a motor for rotation thereby. The centrifugal pump includes a plurality of vanes radiating outwardly from a region adjacent the center of rotation and cover members positions on opposite sides of the vanes. The vanes and cover members cooperate and define flow paths through which medium can be induced to flow due to the centrifugal forces created during rotation of the vanes. The vanes have a distance between respective side boundaries thereof which is less at a position inwardly of the outer disposed end of the vanes than at the outer disposed ends of the vanes.

15 Claims, 4 Drawing Figures

FERMENTATION APPARATUS AND METHOD

The present invention relates to a centrifugal pump having a unique vane configuration. One aspect of the invention relates to such a centrifugal pump mounted in a fermenter for circulation of medium within the fermenter.

In the conducting of certain fermentation processes it is highly desirable to induce circulation of fermentation medium within a fermenter vessel. One particularly advantageous means of inducing such circulation is by the use of a centrifugal pump positioned at one end of a draft tube. Medium flows downwardly through the draft tube and by the centrifugal force applied by the pump the medium is induced to flow outwardly into an annular space between the draft tube and the vessel and upwardly through the annulus for return flow back through the draft tube. Such a fermenter has been found to provide excellent growth characteristics for the microorganisms being cultured in the vessel. In such fermentation processes, a foam can be formed which provides high surface area contact between the liquid phase of the medium and the gaseous phase of the medium to provide high oxygen transfer rates; therefore, the pump must be capable of effectively pumping a foam. It has also been found that the gaseous phase, which is the discontinuous phase of the medium, should be in as finely divided bubbles as possible. Thus, the pump to be even more effective in assisting the fermentation process, should be capable of providing shearing action to the medium to break the gaseous phase bubbles into more finely divided bubbles. It has been proposed to help break up the gaseous phase into smaller bubbles by providing an emulsifying sieve or the like at the outer extremity of the pump.

It has now been found that subjecting the medium to the shearing action of a centrifugal pump and/or an emulsifying sieve can cause the death of or damage to the microorganism being cultivated. This is particularly true of bacteria which are especially susceptible to dying from shearing action. Therefore, the problem is presented of subjecting the fermentation medium to shearing action to break up the gaseous phase into more finely divided bubbles without damaging the microorganism.

In the design of centrifugal pumps such as turbines, one consideration given great weight is the prevention of cavitation. If cavitation occurs, it can cause serious damage to the pump in a very short period of time. Cavitation is a phenomenon which occurs when the total pressure, to which the liquid being pumped is subjected, falls below the vapor pressure of the liquid and a portion of the liquid suddenly becomes vaporous, forming a pocket of vapor. When the total pressure on this vapor rises above the vapor pressure, the vapor suddenly collapses to once again form liquid with the surrounding liquid also rushing in to impinge on portions of the turbine with tremendous force thereby causing damage to the vanes and/or other portions of the turbine. Therefore, in normal pumps it is crucial that the vane design be such to prevent cavitation from occurring. Normally, the faster the velocity of the liquid being pumped between the vanes, the higher the probability that cavitation will occur. Turbines or centrifugal pumps have been designed to limit the amount of divergence of the cross-sectional area from the eye of the impeller to the peripheral outlets between adjacent vanes to keep the total pressure above the liquid vapor pressure. This has been proven to be an effective way of limiting or preventing cavitation. However, in the pumping of foams, cavitation is not such a serious problem because the foam already contains a liquid phase and a gas phase and is not so susceptible to causing caviation.

It is elementary fluid mechanics that flow of a fluid along a tube results in a flow profile which assumes somewhat of a parabolic shape. The maximum velocity is at the center of the flow stream while a zero velocity is present at the tube wall. Therefore, a velocity gradient occurs. Because of the shape of the flow profile, the rate of change of velocity is the greatest adjacent the boundaries of the tubular member and least at the center of the flow stream. This change in velocity is oftentimes referred to as "shear". As discussed above, when a microorganism is contained in the medium and is subjected to shear, damage can be done to the microorganism. Therefore, it would be advantageous to reduce the shear by changing the flow profile to a flatter or less curved profile.

The flow rate of fluid from a turbine is approximated by the equation $$Q = kR^2 h \Omega$$

where k is a constant, R is the turbine radius h is the vane height and $\Omega$ is the turbine rpm. Once Q is established, the fluid continuity condition requires that the radial velocity v follow the equation:

$$v = Q/2\pi r h$$

where r is the distance from the center to the point at which the radial velocity is being measured. Turbulence is proportional to $v^2$ and therefore can be increased by increasing h from the eye of the impeller to its periphery. From the above equation it can be seen that the greater r is, i.e., the distance the center of the turbine, the lower the velocity for a given flow rate and given h.

By providing a centrifugal pump with a vane which has h increasing with increasing r for at least an outer portion of the vane, several advantages can be realized, particularly in fermentation processes. One advantage is that the peripheral velocity of the turbine (at R) can be held low by making h larger at R while maintaining an adequate flow rate. The advantage of such an arrangement is that it avoids excessively high fluid velocity at the periphery of the impeller and consequent shearing of organisms. Another advantage is that a relatively small h adjacent the center of the turbine will produce high shear of the fermentation medium and consequently small bubbles inside the turbine which will result in a minimum of shear effect on the microorganism because of the short exposure time to shear at the locus of the eye. This should also result in less damage to the microorganism.

It is an object of this invention to provide a centrifugal pump which provides high shearing action on a liquid adjacent the eye of the pump while minimizing or reducing shearing action elsewhere in the pump which could damage microorganisms in the liquid being pumped. Another object of the present invention is to provide a centrifugal pump which has a vane with side boundaries which increase in separating distance the further the point of measurement of the height of the vane is from the center of the pump. It is another object of the present invention to provide a fermentation apparatus using a centrfugal pump having a vane which has the distance between side boundaries (h) increase the further the point of measurement of h is from the center of the pump. It is a further object of the present invention to provide a centrifugal pump which is simple in construction and well adapted for its intended use.

Other objects and advantages of the present invention will become apparent from the following detailed description taken in connection with the accompanying drawings wherein are set forth by way of illustration and example certain embodiments of this invention.

Figure 1:
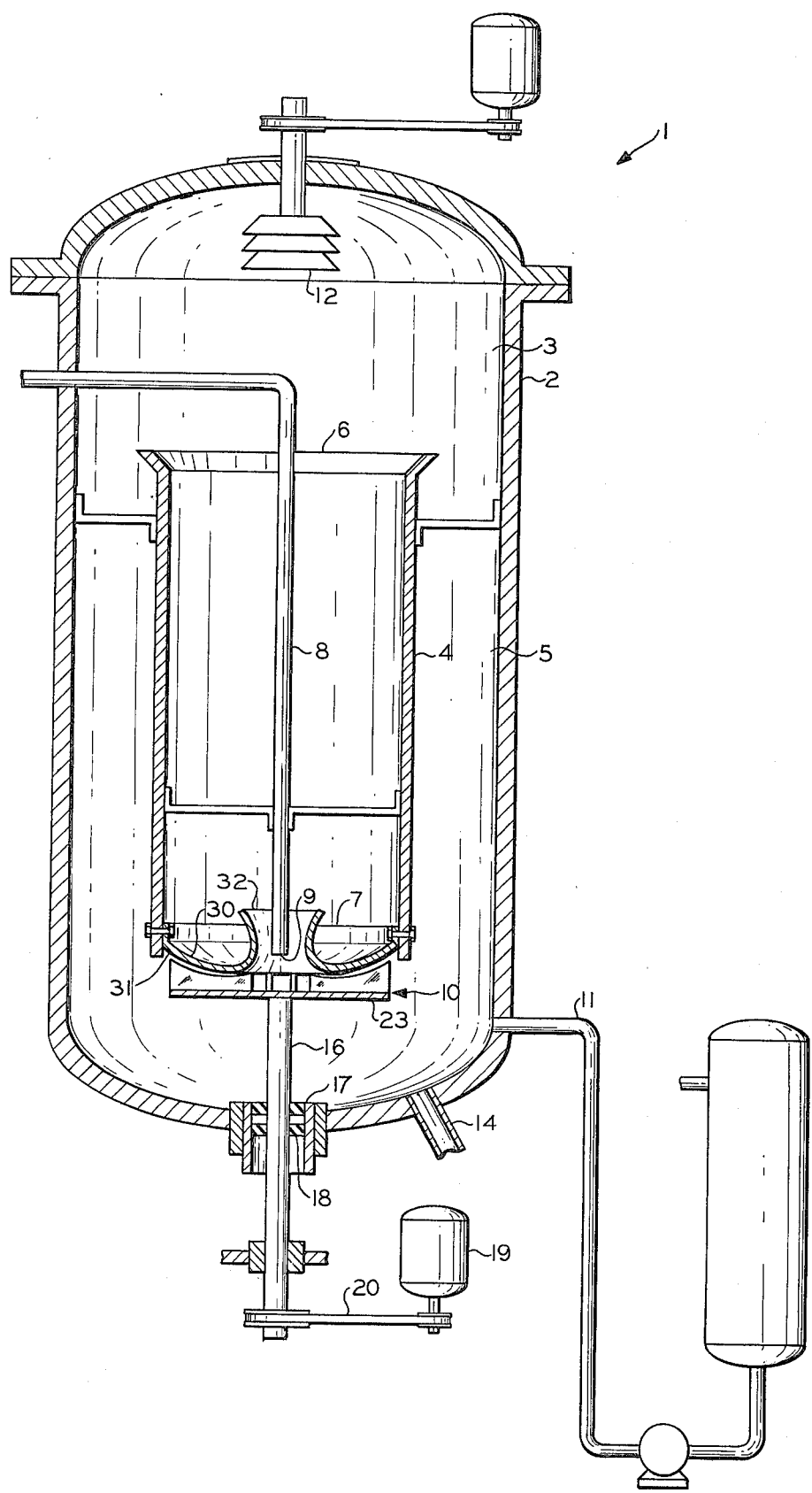
FIG. 1 is a side-sectional view of a fermentation apparatus having a centrifugal pump therein.
Figure 2:
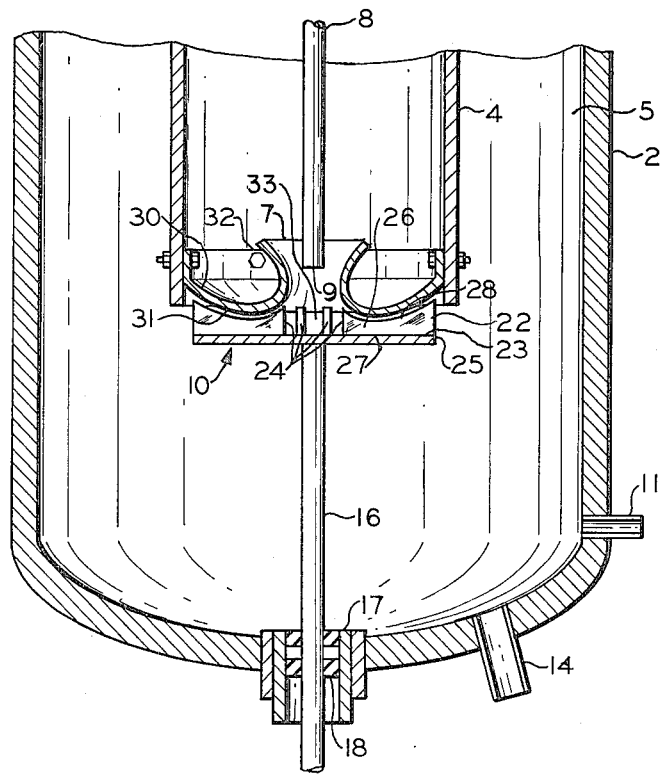
FIG. 2 is an enlarged fragmentary sectional view showing more detail of the centrifugal pump.
Figure 3:
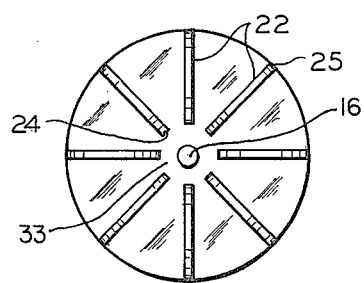
FIG. 3 is a fragmentary plan view of the impeller portion of the centrifugal pump.

The reference numeral 1 designates generally a fermentation apparatus or the like which is comprised of a vessel 2 which defines a fermentation reaction zone or chamber 3 therein. As illustrated, there is positioned within the chamber 3 a draft tube 4 which preferably is generally coaxial with the vessel 2. Both the vessel 2 and tubular member 4 preferably are generally cylindrical. The draft tube 4 is spaced from the interior surface of the vessel 2, forming an annular flow path 5 therebetween. The draft tube 4 preferably has opposite open ends 6 and 7. The apparatus 1 includes an oxygen inlet 8 which opens into the chamber 3 and preferably, the inlet means 8 is an elongate tube and has an outlet end 9 positioned adjacent the eye of a centrifugal pump means or impeller means 10. Also, the apparatus 1 can include an inlet means 11 operable for introducing nutrients and other component parts of the fermentation medium into the chamber 3. There also can be provided a mechanical foam breaker 12 such as that disclosed in U.S. Pat. Nos. 3,693,325 and 3,577,868 which is a centrifugal type. The vessel 2 also has a discharge outlet 14 for discharge of a portion of the contents therein.

The centrifugal pump means 10 includes a shaft 16 which extends through the wall of the vessel 2 and is rotatably mounted in bearings 17. Preferably, the shaft 16 has seal means 18 cooperating therewith to prevent the leakage of the contents of the vessel 2. Motive means 19, such as an electric motor, is operably connected to the shaft by drive means 20 such as a belt and pulley arrangement such that the motor provides the operating power for rotating the shaft 16.

Figure 4:
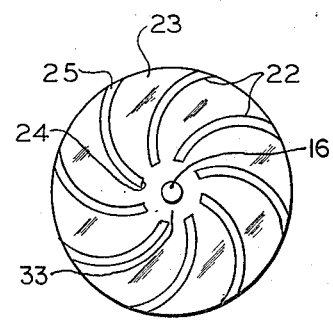
FIG. 4 is a fragmentary plan view of a second embodiment of the centrifugal pump.

The pump means 10 includes a plurality of vanes 22 suitably carried by the shaft 16. In the form shown, the vanes 22 are secured to or are an integral part of a cover member or plate 23 which is secured to the shaft 16 for rotation therewith. The vanes 22 extend or radiate outwardly from a position adjacent the center of rotation of the cover 23 and can extend either generally radially outwardly from adjacent said center by virtue of the vane 22 being straight or can extend in an arcuate path by virtue of the fact that the vanes are generally arcuately shaped in a plane generally parallel to the plane of rotation and thereby extend arcuately outwardly from adjacent said center, as illustrated in FIG. 4. The vanes 22 each have opposite ends 24 and 25 with the ends 24 being innermost disposed and preferably are spaced apart from each other. Preferably the ends 24 are spaced outwardly on cover 23 from a center of rotation, for example, shaft 16, of said cover 23, forming an inlet eye 33 adjacent the through opening 7 in cover 30. The ends 25 are outermost disposed and are spaced apart from each other. Side surfaces 26 extend between the ends 24 and 25 with the surfaces 26 and the plate 23 at least partially defining flow paths 29 between adjacent pairs of vanes 22. The surfaces 26 are partially defined by first and second boundaries, hereinafter referred to as bottom and top boundaries or edges 27 and 28 with the bottom boundary 27 being at the plate 23 and the top boundary 28 being spaced therefrom as herein more fully described. A cover 30 is positioned adjacent the top boundaries 28 and in cooperation with the surfaces 26 and the plate 23 substantially enclose the flow paths 29 between adjacent vanes 22. The cover 30 is spaced slightly from the boundaries 28. It is to be understood however that the cover 30 could be an integral part of or secured to the vanes 22 and cover 23 for rotation therewith. The shape of the bottom surface 31 substantially conforms to the contour of the top boundaries 28. As shown, the cover 30 has the opening 7 therethrough and is secured to the draft tube 4 in any suitable manner. Also, the cover 30 can form the opening 7 by having a contoured tubular portion 32 forming a smooth entry for receipt of fluid from the draft tube 4. The opening 7 preferably is coaxial with the axis of the shaft 16. The tubular member 32 and the open area between the ends 24 of the vanes 22 form the eye of the pump means 10.

The bottom and top boundaries 27 and 28 are positioned relative to one another in a manner such that the distance h between these boundaries increases along at least the outer portion of the vane 22 in the direction that the vanes 22 extend outwardly from the center of rotation of the cover 23 that is, the top and bottom boundaries of each vane are in diverging relation in a direction generally parallel to the longitudinal axis of the shaft 16 from an inner disposed position to an outer disposed position along at least the outer portion of each vane 22. Preferably this outer portion is at least about 50 percent of the vane length. That is, h increases with increasing r, r being the distance the point of measurement is from the center of rotation with h being generally parallel to the longitudinal axis of the shaft 16. Each of the bottom and top boundaries 27 and 28 can be either straight or arcuate so long as the divergence of h along at least an outer portion is present. The maximum distance between the boundaries 27 and 28 is at least about 2 times the minimum distance between the two said boundaries. Preferably, the maximum distance between the boundaries 27 and 28, e.g., at the peripheral outer edge 25 of the vanes 22 is between about 2 times and 10 times the minimum distance between the boundaries 27 and 28, which can be at the innermost edge 24 of the vane 22 or at some intermediate point on the radial length of vanes 22. More preferably, the maximum spacing is between about 3 times and 6 times the minimum spacing. At a position of R, R being the pump 10 radius, the transverse cross-sectional area of the flow path 29 is at least about 4 times and preferably is at least about 15 times the transverse cross-sectional area of the flow path of R/2.

As described above, the vanes 22 can radiate generally radially outwardly from a position adjacent the center of rotation of the cover 23 or can be arcuately shaped that is, the vanes are shaped arcuately in a plane generally parallel to the plane of rotation and thereby extend arcuately outward from adjacent said center. Also, it is to be noted that the inner ends 24 have a boundary spacing greater than the boundary spacing at an intermediate position between the ends 24 and 25. However, it is preferred that the spacing between the top and bottom boundaries 28 and 27 at the inner end 24 be less than the boundary spacing between the top and bottom boundaries 28 and 27 adjacent the outer end 25.

It is to be understood that while there have been illustrated and described certain forms of this invention, it is not to be limited to the specific form or arrangement of parts herein described and shown except to the extent that such limitations or their equivalents are found in the claims.

What is claimed and desired to be secured by Letters Patent is:

1. A fermentation apparatus including:
    a vessel defining a fermentation chamber therein;
    a draft tube mounted in said chamber and having through openings adjacent opposite ends thereof, said draft tube being spaced from an interior surface of said vessel forming a flow path therebetween;
    a shaft having at least a portion thereof positioned in said chamber;
    bearing means rotatably mounting said shaft;
    motive means operably connected to said shaft to effect rotation thereof;
    impeller means positioned in said chamber, said impeller means including a plurality of vanes carried by said shaft and extending outwardly therefrom, adjacent pairs of said plurality of vanes at least partially defining flow paths therefrom, said vanes each having a first end adjacent said shaft and a second end spaced from said shaft outwardly of a respective said first end, said vanes each having first and second boundaries extending between respective first and second ends, said first and second boundaries of each vane being in diverging relation in a direction generally parallel to the longitudinal axis of the shaft from an inner disposed position to an outer disposed position along at least an outer portion of the length of the respective vane wherein the maximum distance spacing between a respective first boundary and a respective second boundary adjacent said second end is at least about 2 times the minimum distance between the first and second boundaries, each said pair of vanes at least partially defining an inlet opening adjacent said respective first ends and an outlet opening adjacent said respective second ends; and
    cover means comprising a first member and a second member, said first member having a respective portion adjacent to said first boundaries of adjacent pairs of said plurality of vanes and said second member having a respective portion adjacent to said second boundaries of adjacent pairs of said plurality of vanes to substantially enclose flow paths between said adjacent pairs of vanes.

2. A fermentation apparatus as set forth in claim 1 wherein:
    said cover means includes a first member secured to said shaft for rotation therewith, said vanes being secured to said first member at their respective first boundaries.

3. A fermentation apparatus as set forth in claim 2 wherein:
    said cover means includes a second member in overlying relation to said vanes and positioned adjacent said second boundaries, said second member having at least one through opening adjacent said first ends.

4. A fermentation apparatus as set forth in claim 3 wherein:
    said first ends are spaced outwardly on said first member from a center of rotation of said first member forming an inlet eye adjacent said second member opening.

5. A fermentation apparatus as set forth in claim 4 wherein:
    said second boundaries are generally straight.

6. A fermentation apparatus as set forth in claim 4 wherein:
    said second boundaries are arcuate.

7. A fermentation apparatus as set forth in claim 4 wherein:
    said vanes extend generally radially outwardly from adjacent said center.

8. A fermentation apparatus as set forth in claim 4 wherein:
    said vanes are shaped arcuately in a plane generally parallel to the plane of rotation and thereby extend arcuately outwardly from the center.

9. A fermentation apparatus as set forth in claim 4 wherein:
    the maximum distance is at least about 3 times the minimum distance.

10. A fermentation apparatus as in claim 4 wherein:
    said oxygen inlet means is an elongate tube; and
    said outlet end of said oxygen inlet means is positioned adjacent said inlet eye of said first member.

11. A fermentation apparatus as in claim 4 wherein:
    said second member opening of said second member of said cover means is adjacent one said through opening of said draft tube to receive fluid therefrom.

12. A fermentation apparatus as in claim 1 further comprising:
    oxygen inlet means having an outlet end opening into said fermentation chamber.

13. A method of pumping fermentation medium including:
    supplying fermentation medium to an inlet zone of a rotating impeller having an axis of rotation;
    flowing fermentation medium from the inlet zone of the rotating impeller along a plurality of flow paths to an outlet zone of the rotating impeller, each of the flow paths having a height (h) which is generally parallel to the axis of rotation of the rotating impeller, the height (h) of each of the flow paths increasing along at least an outer portion of each of the flow paths, and each of the flow paths being substantially enclosed along said at least an outer portion of the flow paths where the height (h) is increasing, the height (h) of each of said flow paths increasing so that the maximum height (h) is at least 2 times the minimum height (h); and
    discharging the fermentation medium from the outlet zone of the rotating impeller.

14. A method as in claim 13 wherein:
    each of said plurality of flow paths is at least partially defined by adjacent pairs of vanes, each of said vanes having a height (h) which is generally parallel to the axis of rotation of a rotating impeller, the height (h) of each vane increasing at least along an outer portion of each of the vanes, and each of the flow paths being substantially enclosed and substantially conforming to said at least an outer portion of the vanes where the height (h) is increasing.

15. A method as set forth in claims 13 or 14 wherein:
    the height (h) of each of said flow paths increases so that the maximum height (h) is at least 3 times the minimum height (h).

* * * * *